US008579880B2

(12) United States Patent
Grady et al.

(10) Patent No.: US 8,579,880 B2
(45) Date of Patent: Nov. 12, 2013

(54) DEVICES AND METHODS FOR MAKING AND ADMINISTERING AN INTRAVENOUS LIQUID WITH SUPERSATURATED DISSOLVED GAS

(75) Inventors: Daniel J. Grady, Weaverville, NC (US); Johnny Harold Riggs, Mocksville, NC (US)

(73) Assignee: Outcome Solutions, LLC, Greensboro, NC (US)

( * ) Notice: Subject to any disclaimer, the term of this patent is extended or adjusted under 35 U.S.C. 154(b) by 0 days.

(21) Appl. No.: 13/410,164

(22) Filed: Mar. 1, 2012

(65) Prior Publication Data

US 2013/0230602 A1 Sep. 5, 2013

(51) Int. Cl.
*A61M 31/00* (2006.01)
*A61M 37/00* (2006.01)
*A61F 7/12* (2006.01)

(52) U.S. Cl.
USPC .............................. 604/507; 604/113; 604/24

(58) Field of Classification Search
USPC ............................ 604/24, 500, 506, 507, 113
See application file for complete search history.

(56) References Cited

U.S. PATENT DOCUMENTS

| 4,919,895 | A | | 4/1990 | Heldebrandt et al. | |
|---|---|---|---|---|---|
| 5,084,011 | A | | 1/1992 | Grady | |
| 5,277,175 | A | | 1/1994 | Riggs et al. | |
| 5,709,654 | A | * | 1/1998 | Klatz et al. | 604/24 |
| 5,827,222 | A | * | 10/1998 | Klatz et al. | 604/507 |
| 6,149,624 | A | * | 11/2000 | McShane | 604/113 |
| 6,149,670 | A | * | 11/2000 | Worthen et al. | 607/3 |
| 6,156,007 | A | * | 12/2000 | Ash | 604/113 |
| 6,336,910 | B1 | * | 1/2002 | Ohta et al. | 604/6.13 |
| 6,393,320 | B2 | * | 5/2002 | Lasersohn et al. | 607/3 |
| 6,537,246 | B1 | | 3/2003 | Unger et al. | |
| 6,589,223 | B1 | * | 7/2003 | Segall et al. | 604/500 |
| 6,818,011 | B2 | * | 11/2004 | Dobak, III | 607/96 |
| 6,899,847 | B2 | * | 5/2005 | Myrick et al. | 422/45 |
| 2004/0058432 | A1 | * | 3/2004 | Owen et al. | 435/284.1 |
| 2004/0158191 | A1 | * | 8/2004 | Samson et al. | 604/6.13 |
| 2007/0286809 | A1 | | 12/2007 | Williams et al. | |
| 2010/0121273 | A1 | * | 5/2010 | Kochanek et al. | 604/113 |
| 2011/0081384 | A1 | | 4/2011 | Archambeau et al. | |

FOREIGN PATENT DOCUMENTS

| WO | 0004943 A1 | 2/2000 |
|---|---|---|
| WO | 2010062628 A1 | 6/2010 |

OTHER PUBLICATIONS

Reiss, Jean G. "Oxygen Carriers ("Blood Substitutes")—Raison D'Etre, Chemistry, and Some Physiology." Chemical Reviews 101: 2797-2919. 2001. American Chemical Society, Washington, DC.
Spiess, Bruce D. "Perfluorocarbon emulsions as a promising technology: a review of tissue and vascular gas dynamics." Journal of Applied Physiology 106: 1444-1452. Jan. 29, 2009. American Physiological Society, Bethesda, MD.

(Continued)

*Primary Examiner* — Victoria P Shumate
(74) *Attorney, Agent, or Firm* — Coats & Bennett, P.L.L.C.

(57) ABSTRACT

Methods and devices for treating patients using high partial pressures of dissolved gas in a liquid. Greater than hyperbaric partial pressures of gas may be dissolved and maintained in the liquid when mixing occurs at ambient pressure. Additional increases in dissolved gas partial pressure may be achieved when the temperature of the liquid is further decreased. The method further includes administering the liquid intravenously via a conventional catheter. Gas exchange occurs due to diffusion upon mixing of the liquid and blood within the vasculature of the patient.

25 Claims, 12 Drawing Sheets

(56) References Cited

OTHER PUBLICATIONS

Grady, Daniel J., et al. "Measurement of In Vitro Changes in Arterial Blood Gases Following Infusion of Supersaturated Dissolved Oxygen Solutions." Abstract. Respiratory Care, Oct. 2011. AARC, Irving, TX.

Grady, Daniel J., et al. "Measurement of Dissolved Oxygen Tension in Fluid Following Supersaturation of Fluid with Oxygen Gas Using a Novel Hyperbaric Tonometer." Abstract. Oct. 2011.

Ostrovksy, Gene. "Low-frequency Ultrasound for Chronic Wounds." 5 pages Posting on MedGadget website. Dec. 4, 2007. http://medgadget.com/2007/12/lowfrequency_ultrasound_for_chronic_wounds.html.

"What is Therapeutic Ultrasound?" Author unknown. 2 pages. Medical Products Online website. http://medicalproductsonline.org/whisthul.html, accessed Feb. 24, 2012.

"Therapeutic Ultrasound." Author unknown. 1 page. Online entry in Wikipedia, the free encyclopedia. http://en.wikipedia.org/wiki/Therapeutic_ultrasound, Accessed Feb. 24, 2012.

Kochanek, Patrick. "The brain, the heart, and therapeutic hypothermia." Cleveland Clinic Journal of Medicine, vol. 76 • Suppl. 2. Apr. 2009. pp. S8-S12.

Jacobshagen, Claudius, et al., "Effects of large volume, ice-cold intravenous fluid infusion on respiratory function in cardiac arrest survivors" Resuscitation 80 (2009) 1223-1228. Elsevier.

Becker, Lance. "Cooling Heads and Hearts Versus Cooling Our Heels." Circulation 2010, 122:679-681. Aug. 2010. American Heart Association, Dallas, TX.

Bernard, Stephen, et al. "Induction of Therapeutic Hypothermia by Paramedics After Resuscitation From Out-of-Hospital Ventricular Fibrillation Cardiac Arrest : A Randomized Controlled Trial" Circulation 2010, 122:737-742. Aug. 2010. American Heart Association, Dallas, TX.

Lanphier, E.H. "Hydrogen Peroxide Infusion vs. Hyperbaric Oxygenation: Theoretical Considerations (Mar. 23, 1963)." Journal of Hyperbaric Medicine, vol. 7, No. 1, 1992. 8 pages. Undersea and Hyperbaric Medical Society. Durham, NC.

Durbin, Jr. , Charles G. "Intravenous Oxygenation and CO2 Removal Device: IVOX." Respiratory Care, vol. 37, No. 2. Feb. 1992. pp. 147-153. AARC, Irving, TX.

Spears, Richard, et al., "Aqueous Oxygen: A Highly O2-Supersaturated Infusate for Regional Correction of Hypoxemia and Production of Hyperoxemia." Circulation, vol. 96, No. 12. Dec. 16, 1997. pp. 4385-4391.

Kim, Won Oak., et al., "Intravenous Oxygenation with Lactated Ringer's Solution." Journal of Korean Medical Science, vol. 2, No. 2, pp. 111-115. Jun. 1987.

Zhao, H., et al., "Investigations on Physiological Basis and Clinical Applications of Hyperoxia Solution for Treatment of Hypoxia." SAARC Journal of Anaesthesia, 2008: 1(2): 149-155.

"Protein shelled microbubbles for intravenous oxygen delivery." Author undeclared. Posting on Flintbox website, Nov. 17, 2011. 2 pages. Wellspring Worldwide, LLC. http://www.flintbox.com/public/project/8914/.

Sanders, Jack., et al., "Intravenous Oxygen and Pulmonary Embolism" Annals of Surgery, Aug. 1947. pp. 208-214. Wolters Kluwer/Lippincott, Williams & Wilkins.

Bourne, Geoffrey, et al., "The Value of Intravenous and Intraperitoneal Administration of Oxygen." Am J. Physiology, vol. 82, pp. 328-334. 1927.

Reissmann, Kurt, et al., "Is Intravenous Oxygen Therapy Possible?" Current Researches in Anesthesia and Analgesia, Nov./Dec. 1953. pp. 426-430. International Anesthesia Research Society, San Francisco, CA.

"Things to Watch: IV Oxygenation: turning blue blood to red" Author unlisted. Posting on VectorOnline website, Children's Hospital, Boston. 1 page. http://www.childrenshospital.org/, Accessed Dec. 7, 2011.

Borden, Mark, et al., "Microbubbles for Intravenous Oxygenation." Online posting. 1 page. http://aiche.confex.com/aiche/2008/techprogram/P132164.HTM. American Institute of Chemical Engineers, Accessed Mar. 9, 2011.

"Hillman and Borden win Career Awards." Author unlisted. Online posting, Columbia University Engineering Dept. Description of Borden's project on microscale bubbles technology for intravenous oxygenation. 1 page. http://www.engineering.columbia.edu/hillman-and-borden-win-career-awards, Accessed. Mar. 9, 2011.

List of Articles and Abstracts on Aqueous Oxygen Therapy. 2 pages. TherOx, Inc. 1999.

* cited by examiner

FIGURE 8a (S1-R1)
Ambient Temp = 67F; Ambient Barometric Pressure = 29.7 in Hg

| Parameter | Pre Infusion | During Infusion | | | | Post Infusion | |
|---|---|---|---|---|---|---|---|
| | | 15 min | 30 min | 45 min | 60 min | 15 min | 30 min |
| Body Wt of Subject (kg) | 11.9 | | | | | | |
| Heart rate (beats per minute) | 159 | 174 | 170 | 167 | 145 | 141 | 127 |
| Blood Pressure | 68/42 | 80/45 | 85/50 | 82/48 | 84/50 | 79/46 | 80/50 |
| Core Temperature (°C) | 36.6 | 36 | 35.8 | 35.5 | 35.1 | 34.7 | 34.4 |
| Mode of Ventilator Operation | PRVC | PRVC | PRVC | PRVC | PRVC | PRVC | PRVC |
| $FiO_2$ | 0.21 | 0.21 | 0.21 | 0.21 | 0.21 | 0.21 | 0.21 |
| $V_t$ (ml) | 84 | 84 | 84 | 84 | 84 | 84 | 84 |
| Respiratory Rate (breaths per minute) | 25 | 25 | 25 | 25 | 25 | 25 | 25 |
| $T_i$ (sec) | 0.6 | 0.6 | 0.6 | 0.6 | 0.6 | 0.6 | 0.6 |
| Positive End Expiratory Pressure (cm $H_2O$) | 6 | 6 | 6 | 6 | 6 | 6 | 6 |
| Arterial Blood Gases | | | | | | | |
| pH | 7.34 | 7.3 | 7.3 | 7.31 | 7.32 | 7.35 | 7.37 |
| $pCO_2$ (mm Hg) | 46 | 48 | 49 | 47 | 45 | 45 | 42 |
| $pO_2$ (mm Hg) | 86 | 88 | 89 | 91 | 98 | 101 | 113 |
| $SaO_2$ (%) | 96 | 96 | 96 | 96 | 97 | 97 | 98 |
| $HCO_3$ (mEq/l) | 24.8 | 23.6 | 23.1 | 23 | 23 | 23.7 | 24 |
| tHB (g/dl) | 9.8 | 8.7 | 8.4 | 8.1 | 7.8 | 7.8 | 7.4 |
| Hct (%) | 30 | 28 | 27 | 26 | 25 | 25 | 24 |
| Lactate (mmol/l) | 1.6 | 2.1 | 2 | 1.6 | 1.3 | 1 | 0.8 |
| $Na^+$ (mEq/l) | 143 | 138 | 138 | 139 | 140 | 140 | 138 |
| $K^+$ (mEq/l) | 3 | 3.1 | 3.2 | 3.1 | 3.2 | 3.2 | 3.6 |
| Glu (mg/dl) | 142 | 144 | 136 | 126 | 128 | 128 | 127 |
| $Ca^{2+}$ (mg/dl) | 1.19 | 1.38 | 1.4 | 1.42 | 1.49 | 1.48 | 1.48 |
| Dissolved $O_2$ Fluid Infusion | | | | | | | |
| IV Flowrate (ml/hr) | | 357 | 357 | 357 | 357 | 357 | 357 |
| pH | 7.32 | | | | | | |
| $pCO_2$ (mm Hg) | 5 | | | | | | |
| $pO_2$ (mm Hg) | >760 | | | | | | |
| Infusate Temp (F) | 44 | | | | | | |
| VE | 2.1 | 2.1 | 2.1 | 2.1 | 2.1 | 2.1 | 2.1 |
| Pulmonary Mechanics | | | | | | | |
| $VCO_2$ (ml/min) | 62 | 73 | 78 | 62 | 75 | 56 | 56 |
| Cdyn (ml/cm $H_2O$) | 10 | 15 | 11 | 10 | 11 | 11 | 11 |
| $EtCO_2$ | 44 | 48 | 46 | 44 | 42 | 40 | 39 |
| Vd/VT Airway | | | | | | | |
| Vd Alv | 43 | 46 | 50 | 45 | 48 | 43 | 43 |

FIGURE 8b (S2-R1)
Ambient Temp = 71F; Ambient Barometric Pressure = 29.7 in Hg

| Parameter | Pre Infusion | During Infusion | | | | Post Infusion | |
|---|---|---|---|---|---|---|---|
| | | 15 min | 30 min | 45 min | 60 min | 15 min | 30 min |
| Body Wt of Subject (kg) | 13.2 | | | | | | |
| Heart rate (beats per minute) | 197 | 170 | 169 | 152 | 146 | 152 | 162 |
| Blood Pressure | 66/40 | 74/42 | 80/45 | 80/46 | 85/53 | 89/52 | 94/64 |
| Core Temperature (°C) | 38.5 | 37.2 | 36.8 | 36.3 | 35.9 | 35.7 | 35.5 |
| Mode of Ventilator Operation | PRVC | PRVC | PRVC | PRVC | PRVC | PRVC | PRVC |
| $FiO_2$ | 0.21 | 0.21 | 0.21 | 0.21 | 0.21 | 0.21 | 0.21 |
| $V_t$ (ml) | 93 | 93 | 93 | 93 | 93 | 93 | 93 |
| Respiratory Rate (breaths per minute) | 24 | 24 | 24 | 24 | 24 | 24 | 24 |
| $T_i$ (sec) | 0.6 | 0.6 | 0.6 | 0.6 | 0.6 | 0.6 | 0.6 |
| Positive End Expiratory Pressure (cm $H_2O$) | 5 | 5 | 5 | 5 | 5 | 5 | 5 |
| Arterial Blood Gases | | | | | | | |
| pH | 7.39 | 7.39 | 7.4 | 7.4 | 7.42 | 7.43 | 7.43 |
| $pCO_2$ (mm Hg) | 50 | 49 | 46 | 47 | 46 | 46 | 45 |
| $pO_2$ (mm Hg) | 81 | 89 | 98 | 96 | 102 | 102 | 103 |
| $SaO_2$ (%) | 96 | 97 | 98 | 97 | 98 | 98 | 98 |
| $HCO_3$ (mEq/l) | 28.7 | 28.2 | 27.5 | 28 | 28.8 | 29.3 | 28.9 |
| tHB (g/dl) | 7.4 | 7.1 | 6.8 | 6.5 | 6.5 | 7.4 | 7.4 |
| Hct (%) | 24 | 23 | 22 | 21 | 21 | 24 | 24 |
| Lactate (mmol/l) | 2.4 | 3 | 3 | 2.8 | 2.7 | 2 | 2.3 |
| $Na^+$ (mEq/l) | 139 | 137 | 137 | 137 | 137 | 137 | 136 |
| $K^+$ (mEq/l) | 3.1 | 3 | 3 | 3 | 3.1 | 3.3 | 3.5 |
| Glu (mg/dl) | 129 | 128 | 120 | 116 | 110 | 115 | 125 |
| $Ca^{2+}$ (mg/dl) | 1.4 | 1.41 | 1.4 | 1.43 | 1.4 | 1.5 | 1.45 |
| Dissolved $O_2$ Fluid Infusion | | | | | | | |
| IV Flowrate (ml/hr) | 396 | 396 | 396 | 396 | 396 | 10 | 10 |
| pH | 7.35 | | | | | | |
| $pCO_2$ (mm Hg) | 5 | | | | | | |
| $pO_2$ (mm Hg) | >760 | | | | | | |
| Pulmonary Mechanics | | | | | | | |
| $VCO_2$ (ml/min) | 79 | 75 | 73 | 70 | 65 | 62 | 62 |
| Cdyn (ml/cm $H_2O$) | 10 | 11 | 12 | 11 | 11 | 11 | 11 |
| $EtCO_2$ | 49 | 46 | 45 | 43 | 41 | 41 | 41 |
| Vd/VT Airway | 0.42 | 0.42 | 0.42 | 0.46 | 0.47 | 0.5 | 0.48 |
| Vd Alv | 51 | 50 | 52 | 50 | 48 | 47 | 47 |
| VE | | 2.4 | 2.3 | 2.3 | 2.3 | 2.3 | 2.3 |

FIGURE 8c (S4-R1)
Ambient Temp = 70F; Ambient Barometric Pressure = 759 mm Hg

| Parameter | Pre Infusion | During Infusion | | | | Post Infusion | |
|---|---|---|---|---|---|---|---|
| | | 15 min | 30 min | 45 min | 60 min | 15 min | 30 min |
| Body Wt of Subject (kg) | 14.2 | | | | | | |
| Heart rate (beats per minute) | 128 | 140 | 142 | 139 | 138 | 143 | 141 |
| Blood Pressure | 78/39 | 85/44 | 90/50 | 100/61 | 100/62 | 98/60 | 101/64 |
| Core Temperature (°C) | 37.8 | 37.2 | 37.1 | 37 | 36.7 | 36.5 | 36.7 |
| Mode of Ventilator Operation | PRVC | PRVC | PRVC | PRVC | PRVC | PRVC | PRVC |
| $FiO_2$ | 0.21 | 0.21 | 0.21 | 0.21 | 0.21 | 0.21 | 0.21 |
| $V_t$ (ml) | 100 | 100 | 100 | 100 | 100 | 100 | 100 |
| Respiratory Rate (breaths per minute) | 25 | 25 | 25 | 25 | 25 | 25 | 25 |
| $T_i$ (sec) | 0.6 | 0.6 | 0.6 | 0.6 | 0.6 | 0.6 | 0.6 |
| Positive End Expiratory Pressure (cm $H_2O$) | 5 | 5 | 5 | 5 | 5 | 5 | 5 |
| Arterial Blood Gases | | | | | | | |
| pH | 7.35 | 7.38 | 7.38 | 7.39 | 7.4 | 7.43 | 7.43 |
| $pCO_2$ (mm Hg) | 55 | 51 | 52 | 50 | 49 | 46 | 47 |
| $pO_2$ (mm Hg) | 81 | 89 | 88 | 90 | 93 | 96 | 93 |
| $SaO_2$ (%) | 95 | 97 | 97 | 97 | 97 | 98 | 97 |
| $HCO_3$ (mEq/l) | 28.3 | 28.6 | 29 | 28.8 | 28.9 | 29.3 | 31.2 |
| tHB (g/dl) | 6.5 | 6.2 | 6.2 | 6.2 | 6.2 | 6.5 | 6.5 |
| Hct (%) | 21 | 20 | 20 | 20 | 20 | 21 | 21 |
| Lactate (mmol/l) | 1.5 | 1.8 | 1.7 | 1.6 | 1.5 | 1.3 | 1.2 |
| $Na^+$ (mEq/l) | 137 | 137 | 138 | 137 | 138 | 137 | 136 |
| $K^+$ (mEq/l) | 3.8 | 3.6 | 3.6 | 3.6 | 3.6 | 3.7 | 3.8 |
| Glu (mg/dl) | 110 | 102 | 100 | 95 | 94 | 100 | 102 |
| $Ca^{2+}$ (mg/dl) | 1.37 | 1.38 | 1.39 | 1.37 | 1.41 | 1.44 | 1.4 |
| Dissolved $O_2$ Fluid Infusion | | | | | | | |
| IV Flowrate (ml/hr) | 426 | 426 | 426 | 426 | 426 | 426 | 426 |
| pH | 7.35 | | | | | | |
| $pCO_2$ (mm Hg) | 5 | | | | | | |
| $pO_2$ (mm Hg) | >760 | | | | | | |
| Infusate Temp (°F) | 53 | 50 | 49 | 48 | 49 | 49 | 49 |
| SAT | 94 | 94 | 94 | 94 | 94 | 94 | 95 |
| Pulmonary Mechanics | | | | | | | |
| $VCO_2$ (ml/min) | 83 | 78 | 77 | 75 | 74 | 71 | 70 |
| Cdyn (ml/cm $H_2O$) | 13 | 12 | 12 | 11 | 11 | 11 | 12 |
| $EtCO_2$ | 53 | 49 | 48 | 47 | 45 | 45 | 44 |
| Vd/VT Airway | 0.47 | 0.47 | 0.48 | 0.48 | 0.47 | 0.47 | 0.48 |
| Vd Alv | 50 | 50 | 51 | 50 | 50 | 49 | 49 |
| VE | 2.6 | 2.6 | 2.6 | 2.6 | 2.5 | 2.5 | 2.5 |

FIGURE 8d (S5-R1)
Ambient Temp = 70F; Ambient Barometric Pressure = 760 mm Hg

| Parameter | Pre Infusion | During Infusion | | | | Post Infusion | |
|---|---|---|---|---|---|---|---|
| | | 15 min | 30 min | 45 min | 60 min | 15 min | 30 min |
| Body Wt of Subject (kg) | 12.2 | | | | | | |
| Heart rate (beats per minute) | 135 | 127 | 123 | 117 | 115 | 114 | 116 |
| Blood Pressure | 86/47 | 96/54 | 99/57 | 100/60 | 101/62 | 100/62 | 103/67 |
| Core Temperature (°C) | 38 | 37.1 | 36.7 | 36.2 | 35.9 | 35.6 | 35.5 |
| Mode of Ventilator Operation | PRVC | PRVC | PRVC | PRVC | PRVC | PRVC | PRVC |
| $FiO_2$ | 0.21 | 0.21 | 0.21 | 0.21 | 0.21 | 0.21 | 0.21 |
| $V_t$ (ml) | 86 | 86 | 86 | 86 | 86 | 86 | 86 |
| Respiratory Rate (breaths per minute) | 25 | 25 | 25 | 25 | 25 | 25 | 25 |
| $T_i$ (sec) | 0.6 | 0.6 | 0.6 | 0.6 | 0.6 | 0.6 | 0.6 |
| Positive End Expiratory Pressure (cm $H_2O$) | 5 | 5 | 5 | 5 | 5 | 5 | 5 |
| Arterial Blood Gases | | | | | | | |
| pH | 7.4 | 7.43 | 7.43 | 7.42 | 7.44 | 7.46 | 7.47 |
| $pCO_2$ (mm Hg) | 49 | 46 | 45 | 47 | 45 | 44 | 44 |
| $pO_2$ (mm Hg) | 76 | 90 | 95 | 98 | 99 | 102 | 103 |
| $SaO_2$ (%) | 95 | 97 | 98 | 98 | 98 | 98 | 98 |
| $HCO_3$ (mEq/l) | 28.8 | 29.3 | 29 | 29.3 | 29.6 | 30.3 | 30.9 |
| tHB (g/dl) | 7.4 | 8.5 | 6.5 | 6.8 | 6.2 | 6.5 | 6.8 |
| Hct (%) | 24 | 21 | 21 | 22 | 20 | 20 | 22 |
| Lactate (mmol/l) | 1.2 | 1.5 | 1.5 | 1.3 | 1.5 | 1.3 | 1.1 |
| $Na^+$ (mEq/l) | 138 | 138 | 138 | 138 | 138 | 137 | 137 |
| $K^+$ (mEq/l) | 3.6 | 3.4 | 3.4 | 3.4 | 3.4 | 3.5 | 3.7 |
| Glu (mg/dl) | 114 | 93 | 91 | 85 | 85 | 85 | 91 |
| $Ca^{2+}$ (mg/dl) | 1.32 | 1.36 | 1.38 | 1.39 | 1.38 | 1.38 | 1.45 |
| Dissolved $O_2$ Fluid Infusion | | | | | | | |
| IV Flowrate (ml/hr) | 366 | 366 | 366 | 366 | 366 | 366 | 366 |
| pH | 7.35 | | | | | | |
| $pCO_2$ (mm Hg) | 5 | | | | | | |
| $pO_2$ (mm Hg) | >760 | | | | | | |
| Infusate Temp (°F) | 50 | 50 | 50 | 50 | 49 | 49 | 49 |
| Pulmonary Mechanics | | | | | | | |
| $VCO_2$ (ml/min) | 70 | 67 | 64 | 64 | 61 | 58 | 57 |
| Cdyn (ml/cm $H_2O$) | 11 | 11 | 10 | 9 | 10 | 10 | 10 |
| $EtCO_2$ | 48 | 45 | 43 | 43 | 41 | 40 | 39 |
| Vd/VT Airway | 0.42 | 0.41 | 0.41 | 0.46 | 0.46 | 0.47 | 0.47 |
| Vd Alv | 44 | 45 | 44 | 44 | 45 | 45 | 44 |

FIGURE 8e (S3-R1)
Ambient Temp = 71F; Ambient Barometric Pressure = 29.9 mm Hg

| Parameter | Pre Infusion | During Infusion | | | |
|---|---|---|---|---|---|
| | | 15 min | 30 min | 45 min | 60 min |
| Body Wt of Subject (kg) | 13.45 | | | | |
| Heart rate (beats per minute) | 167 | 162 | 169 | 170 | 178 |
| Blood Pressure | 78/40 | 85/45 | 84/45 | 97/57 | |
| Core Temperature (°C) | 38.4 | 38.2 | 37.9 | 37.7 | 37.6 |
| Mode of Ventilator Operation | PRVC | PRVC | PRVC | PRVC | PRVC |
| $FiO_2$ | 0.21 | 0.21 | 0.21 | 0.21 | 0.21 |
| $V_t$ (ml) | 95 | 95 | 95 | 95 | 95 |
| Respiratory Rate (breaths per minute) | 25 | 25 | 25 | 25 | 25 |
| $T_i$ (sec) | 0.6 | 0.6 | 0.6 | 0.6 | 0.6 |
| Positive End Expiratory Pressure (cm $H_2O$) | 5 | 5 | 5 | 5 | 5 |
| Arterial Blood Gases | | | | | |
| pH | 7.34 | 7.38 | 7.39 | 7.4 | 7.4 |
| $pCO_2$ (mm Hg) | 50 | 47 | 44 | 45 | 46 |
| $pO_2$ (mm Hg) | 68 | 74 | 76 | 80 | 75 |
| $SaO_2$ (%) | 92 | 94 | 95 | 96 | 95 |
| $HCO_3$ (mEq/l) | 27 | 27 | 26 | 27 | 27.6 |
| tHB (g/dl) | 6.8 | 6.5 | 6.2 | 6.8 | 6.5 |
| Hct (%) | 22 | 21 | 20 | 22 | 21 |
| Lactate (mmol/l) | 2.6 | 2.4 | 2.7 | 2.4 | 2.4 |
| $Na^+$ (mEq/l) | 135 | 134 | 136 | 137 | 135 |
| $K^+$ (mEq/l) | 3.8 | 3.6 | 3.7 | 3.7 | 3.6 |
| Glu (mg/dl) | 132 | 121 | 110 | 116 | 107 |
| $Ca^{2+}$ (mg/dl) | 1.32 | 1.32 | 1.33 | 1.35 | 1.32 |
| Dissolved $O_2$ Fluid Infusion | | | | | |
| IV Flowrate (ml/hr) | 405 | 405 | 405 | 405 | 405 |
| pH | 7.35 | | | | |
| $pCO_2$ (mm Hg) | 5 | | | | |
| $pO_2$ (mm Hg) | 203 | | | | |
| Infusate Temp (°F) | 71 | | | | |
| Pulmonary Mechanics | | | | | |
| $VCO_2$ (ml/min) | 94 | 87 | 85 | 82 | 82 |
| Cdyn (ml/cm $H_2O$) | 10 | 10 | 10 | 10 | 10 |
| $EtCO_2$ | 53 | 49 | 47 | 47 | 46 |
| Vd/VT Airway | 0.34 | 0.34 | 0.35 | 0.35 | 0.36 |
| Vd Alv | 56 | 57 | 57 | 55 | 57 |
| VE | 16 | 16 | 13 | 12 | 11 |

FIGURE 8f (S3-R2)

Ambient Temp = 71F; Ambient Barometric Pressure = 29.9 mm Hg

| Parameter | Pre Infusion | During Infusion | | | |
|---|---|---|---|---|---|
| | | 15 min | 30 min | 45 min | 60 min |
| Body Wt of Subject (kg) | 13.4 | | | | |
| Heart rate (beats per minute) | 184 | | | | |
| Blood Pressure | 102/68 | 103/71 | 105/73 | 111/79 | 116/85 |
| Core Temperature (°C) | 37.6 | 37.3 | 37.1 | 36.8 | 36.5 |
| Mode of Ventilator Operation | PRVC | PRVC | PRVC | PRVC | PRVC |
| $FiO_2$ | 0.21 | 0.21 | 0.21 | 0.21 | 0.21 |
| $V_t$ (ml) | 95 | 95 | 95 | 95 | 95 |
| Respiratory Rate (breaths per minute) | 25 | 25 | 25 | 25 | 25 |
| $T_i$ (sec) | 0.6 | 0.6 | 0.6 | 0.6 | 0.6 |
| Positive End Expiratory Pressure (cm $H_2O$) | 5 | 5 | 5 | 5 | 5 |
| Arterial Blood Gases | | | | | |
| pH | 7.4 | 7.44 | 7.44 | 7.44 | 7.45 |
| $pCO_2$ (mm Hg) | 46 | 45 | 44 | 44 | 43 |
| $pO_2$ (mm Hg) | 75 | 79 | 79 | 83 | 80 |
| $SaO_2$ (%) | 95 | 96 | 96 | 97 | 96 |
| $HCO_3$ (mEq/l) | | 29.5 | 29.1 | 29.1 | 29.2 |
| tHB (g/dl) | | 6.5 | 6.5 | 5.9 | 6.2 |
| Hct (%) | | 21 | 21 | 19 | 20 |
| Lactate (mmol/l) | | 1.8 | 1.6 | 1.6 | 1.5 |
| $Na^+$ (mEq/l) | | 133 | 134 | 133 | 135 |
| $K^+$ (mEq/l) | | 3.7 | 3.8 | 3.9 | 3.9 |
| Glu (mg/dl) | | 111 | 105 | 109 | 118 |
| $Ca^{2+}$ (mg/dl) | | 1.31 | 1.34 | 1.32 | 1.34 |
| Dissolved $O_2$ Fluid Infusion | | | | | |
| IV Flowrate (ml/hr) | 405 | 405 | 405 | 405 | 405 |
| pH | 7.35 | | | | |
| $pCO_2$ (mm Hg) | 5 | | | | |
| $pO_2$ (mm Hg) | >760 | | | | |
| Infusate Temp (°F) | 47 | | | | |
| SAT | 92 | 94 | 96 | 92 | 92 |
| Pulmonary Mechanics | | | | | |
| $VCO_2$ (ml/min) | 82 | 80 | 77 | 76 | 73 |
| Cdyn (ml/cm $H_2O$) | 9 | 9 | 9 | 8 | 8 |
| $EtCO_2$ | 46 | 43 | 42 | 41 | 40 |
| Vd/VT Airway | 0.34 | 0.37 | 0.38 | 0.38 | |
| Vd Alv | 58 | 1.4 | 1.4 | 1.4 | 1.4 |
| VE | 2.5 | 2.4 | 2.4 | 2.4 | 2.4 |

DEVICES AND METHODS FOR MAKING AND ADMINISTERING AN INTRAVENOUS LIQUID WITH SUPERSATURATED DISSOLVED GAS

BACKGROUND

Multiple cardiopulmonary diseases result in tissue hypoxia, which is a deficiency of molecular oxygen available for cellular metabolism. Conditions such as influenza, asthma, pneumonia, and the adult respiratory distress syndrome are examples of diseases which may produce tissue hypoxia because of complex pathology within the lung. Treatment of hypoxia is conventionally directed at the cause of hypoxia. For example, when hypoxia is caused by deficiencies in the partial pressure of oxygen in inspired gas diffusing across the alveolar capillary membrane in the lung, conventional treatment involves increasing the partial pressure of inspired oxygen in the inspired atmosphere.

Increasing the partial pressure of inspired oxygen may be accomplished via multiple breathing devices such as masks, nasal cannula, endotracheal tubes, tracheostomy tubes, mechanical ventilators. In essence, the purpose of oxygen inhalation is to increase the quantity of oxygen absorbed into the blood in hopes of improving oxygen delivery to cells and tissues. Traditional methods of oxygen therapy involve the inhalation of gaseous oxygen. These methods, however, are associated with several complications and limitations. First, if the breathing passages are blocked or if a person has stopped breathing altogether, inadequate amounts of oxygen are absorbed into the bloodstream to sustain cellular metabolism. Second, gaseous oxygen inhalation may be toxic to tissues if inhaled in high concentrations over prolonged periods. Third, inhalation of high concentrations of gaseous oxygen causes atelectasis, or lung collapse.

Other methods and processes have been developed to improve oxygen delivery to tissues. For instance, hyperbaric breathing chambers involve the placement of a person inside a sealed chamber with the subsequent pressurization of the chamber. During chamber pressurization, the patient inhales gaseous oxygen through normal respiratory channels which results in increased blood oxygen levels. However, multiple limitations exist for this method of oxygen therapy. For example, the breathing chambers are extremely expensive and complex facilities, and highly trained personnel are needed for safe operation. Further, the increased blood oxygen levels achieved during chamber pressurization and oxygen inhalation are lost when the chamber is de-pressurized and the person is removed from the chamber. Numerous complications have been documented with this method of oxygen therapy, including fires, explosions, oxygen toxicity, gas embolism, and Caisson's disease from rapid chamber de-pressurization.

Another traditional method of delivering oxygen to tissues is via intravenous injection of gaseous oxygen. This method has been found to be extremely hazardous, as gas bubbles tend to coalesce in the veins and occlude smaller pulmonary arteries. The resulting gaseous pulmonary embolism causes a decreased pulmonary circulation, arterial hypoxemia, and systemic hypoxia. Due to the extreme hazards, this method of oxygen therapy is generally considered to have little, if any, practical utility.

Maintaining proper carbon dioxide levels in the human body is similarly important. It is not uncommon that a patient experiencing lower levels of oxygen simultaneously experiences heightened carbon dioxide levels. For example, carbon dioxide retention may occur with hypoxemia in patients suffering from chronic obstructive pulmonary disease (COPD). This can be especially problematic as one of the treatments for COPD is supplemental oxygen therapy, which can itself lead to heightened carbon dioxide levels.

SUMMARY

The present application includes methods and devices for dissolving gas in a non-blood intravenous liquid using hyperbaric tonometry. The aspects provide for mixing at ambient pressure a gas and a cooled liquid. In one embodiment, gas partial pressures greater than 760 mm. Hg may be dissolved and retained in the liquids when mixed at ambient pressure and a decreased temperature.

The present application also includes methods and devices for decreasing the temperature of a liquid prior to and/or during the process of mixing the liquid with a gas resulting in hyperbaric gas partial pressures retained within the liquid. The increased gas partial pressures combined with the decreased temperature of the liquid may be used for induction of therapeutic hypothermia and may be useful as a resuscitation liquid.

The present application includes that liquid may be supersaturated with gas partial pressures and achieve hyperbaric gas partial pressures in the liquid by decreasing the temperature of the gas-liquid contact device thereby increasing the solubility of the liquid for the process of gas solvation. The temperature decrease of the gas and liquid allows gas partial pressures to remain dissolved in liquid at greater levels than hyperbaric pressure (hyperbaric is defined as pressure greater than 760 mm Hg., or 1 atmosphere) when mixed at ambient pressure. In some embodiments, the range of partial pressures generated is about 500 mm Hg. to about 1000 mm Hg.

The application also includes that for gas partial pressures greater than 1000 mm Hg., a pressurized gas-liquid contact device may be used to apply additional pressure greater than 1 atmosphere.

One embodiment disclosed in the present application is a method of treating a patient. The method includes intravenously infusing into the patient a non-blood liquid supersaturated with oxygen gas, and maintaining the supersaturated liquid at a low temperature while infusing the liquid into the patient so as to decrease a core body temperature of the patient from a pre-infusion baseline temperature to induce mild therapeutic hypothermia in the patient.

The liquid may be at ambient pressure while being intravenously infused into the patient. The liquid may be less than about 70° F. while being intravenously infused into the patient. The supersaturated liquid may increase oxygen delivery to tissue while simultaneously decreasing tissue metabolic rate of oxygen consumption and carbon dioxide production. The intravenous infusion of the supersaturated liquid may induce mild therapeutic hypothermia, producing intravascular gas exchange and increases the chemical affinity between hemoglobin and dissolved oxygen.

The application also includes a method of treating a patient that includes supersaturating an intravenous non-blood liquid with dissolved oxygen gas. The method includes decreasing the temperature of the liquid and increasing a concentration of the gas dissolved in the liquid. The method also includes infusing the supersaturated liquid at the decreased temperature intravenously into the patient to decrease a core body temperature of the patient from a pre-infusion baseline temperature so as to induce mild therapeutic hypothermia.

In this method, decreasing the temperature of the liquid may include decreasing the temperature to less than about 55° F. Supersaturating the liquid with the dissolved oxygen gas may occur at ambient pressure. Supersaturating the liquid with the dissolved oxygen gas may occur within an IV bag.

Another method is directed to intravenous liquid therapy. The method includes mixing a gas with a non-blood liquid while the non-blood liquid is at a decreased temperature of less than about 55° F. and at ambient pressure. The method includes maintaining the liquid in contact with the gas at ambient pressure and at less than about 55° F. until the partial pressure of the gas in the liquid reaches at least 760 mmHg. The method also includes intravenously introducing the liquid into a patient while maintaining the liquid at less than about 55° F. and the partial pressure of the gas of at least 760 mm Hg.

The method may also include initially introducing the gas into the liquid when the liquid is less than about 55° F. The gas may be a mixture of two or more different gases. The gas may be selected from the group consisting essentially of oxygen, helium, ozone, and carbon monoxide. The decreased temperature may be less than about 45° F.

Another method is directed to treating a patient. The method includes containing a non-blood liquid at ambient pressure in a container, and introducing a gas into the liquid through a first tube and bubbling the gas through the liquid, the liquid being at a temperature of less than about 55° F. The method includes maintaining the liquid in contact with the gas at the ambient pressure and the liquid at less than about 55° F. until a partial pressure of the gas in the liquid is at least 760 mm Hg. The method includes removing the liquid from the container. The method also includes intravenously introducing the liquid into the patient while maintaining the liquid at less than about 55° F. and the partial pressure of the gas of at least 760 mm Hg.

The method may also include activating a refrigeration unit and reducing the liquid to less than about 55° F. after introducing the gas into the liquid. The method may include cooling the liquid between when the liquid is removed form the container and intravenously introducing into the patient.

The application is also directed to a device for attaching within an outlet of an intravenous liquid container and for mixing a gas with a liquid contained in the container. The device includes a body configured to fit within the outlet of the container, with the body including a leading end configured to be positioned within the container, a trailing end configured to be positioned on an exterior of the container, and first, second, and third ports that extend through the body with each including a first end and a second end with the first end in closer proximity to the leading end of the body than the second end. The device includes a first tube positioned in the first port to introduce a gas into the container. The device also includes a second tube positioned in the second port to remove excessive amounts of the gas from the container.

The first tube may be movable within the first port for an end of the first tube to be movable outward from the first port beyond the leading end of the body. The second tube may be movable within the second port for an end of the second tube to be movable outward from the second port beyond the leading end of the body and outward beyond the first tube. The device may also include a sheath that extends around a portion of one of the first and second tubes that extends outward from the body on the exterior of the container. The leading end of the body may include a pointed tip to facilitate insertion into the outlet of the container.

The various aspects of the various embodiments may be used alone or in any combination, as is desired.

BRIEF DESCRIPTION OF THE DRAWINGS

FIGS. 8a-8f are charts of test subjects that illustrate improvement in blood gases using the invention.

DETAILED DESCRIPTION

Figure 1:
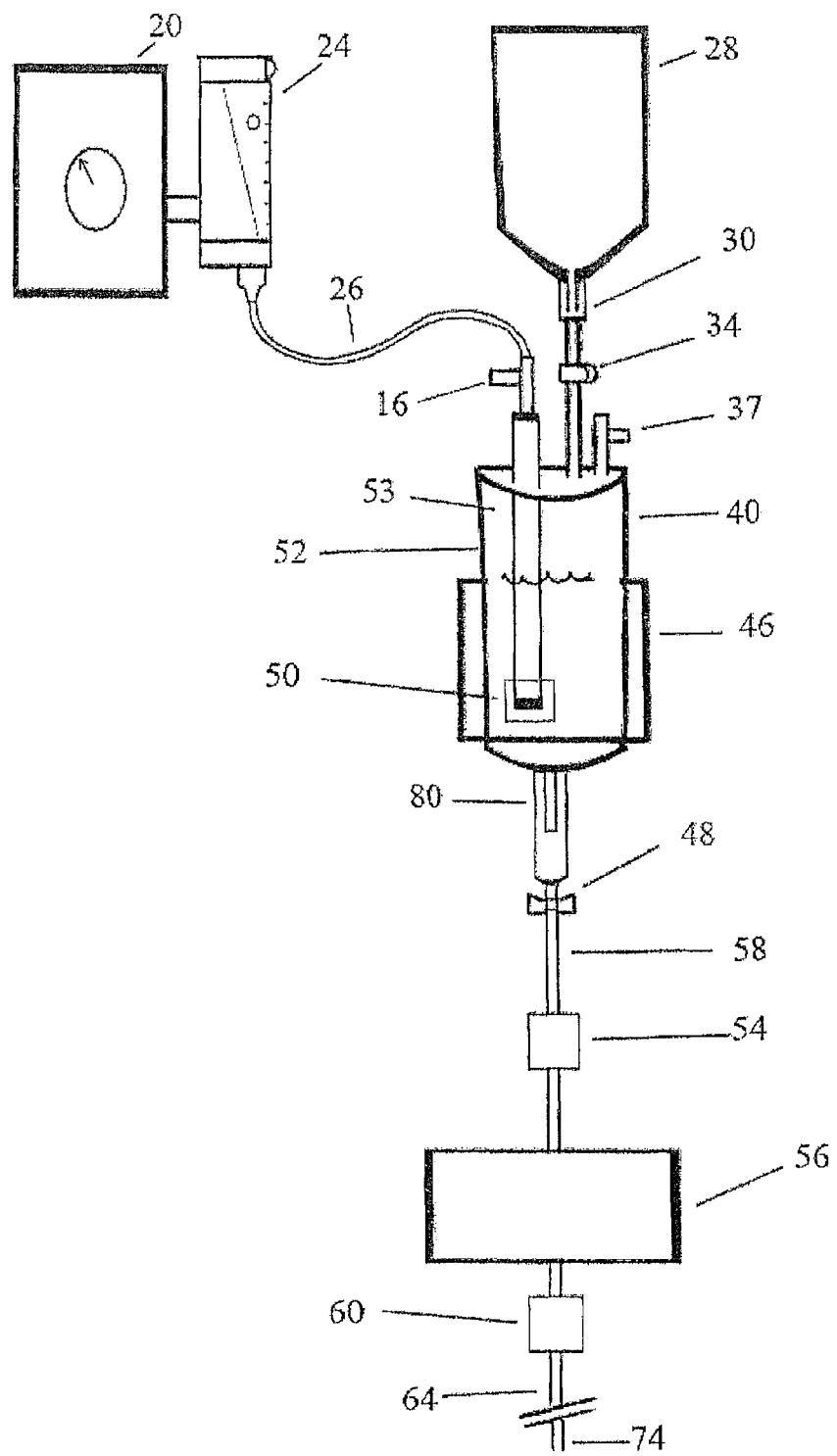
FIG. 1 is a schematic view of a system for dissolving a gas in a cooled liquid at ambient pressure.

The present application is directed to methods and devices for forming liquids having high partial pressures of dissolved gas, and treating patients with the liquids. The liquid with the dissolved gas is formed by contacting a gas with a cooled liquid. It has been found that greater than hyperbaric partial pressures of gas may be dissolved and maintained in the liquid when mixing occurs at ambient pressure. Additional increases in dissolved gas partial pressure may be achieved when the temperature of the liquid is further decreased. The method further includes administering the liquid intravenously via a conventional catheter. Gas exchange occurs due to diffusion upon mixing of the liquid and blood within the vasculature of the patient.

In general, the methods include selection of the desired gas partial pressure to dissolve in a patient's intravenous liquid, solvation of the gas into the liquid, and regulation of the liquid infusion into the vasculature of the patient. The system may be used to mix gas with intravenous liquids at ambient barometric pressure to create hyperbaric dissolved gas partial pressures for individual patient requirements. The supersaturated intravenous liquid that contains hyperbaric levels of dissolved gas, may be administered to a patient to for a variety of different medical purposes.

The methods and devices provide for many different applications and contexts of use. Examples include but are not limited to: use at a patient bedside to mix medical gas with conventional intravenous liquids and customize the resulting liquid to the specific patient needs; emergency trauma situations to rapidly administer high levels of dissolved gas in liquids for conditions of airway obstruction or cardiac arrest; military medical procedures in the field to stabilize a critically injured patient; use as a microbicidal agent for treatment of infections; and oxygen therapy for therapeutic use and rescue oxygenation treatment for diseases such as influenza, ARDS, asthma, and other diseases that produce hypoxemic respiratory failure.

In general, the intravenous liquid methods and devices may treat a patient with a liquid containing hyperbaric partial pressure of dissolved gas. One method includes: (1) mixing a non-blood liquid with gas at ambient barometric pressure in a gas-liquid contact device such that the gas dissolves within the liquid; (2) maintaining the liquid in contact with the gas in the gas-liquid contact device until the partial pressure of the gas reaches a selected hyperbaric partial pressure to produce a supersaturated liquid having the selected hyperbaric pressure; and (3) delivering the supersaturated liquid to a patient. The temperature of the liquid may be decreased before and/or during and/or after contact with the gas to increase the amount of dissolved gas. Further, the temperature of the liquid is maintained at a lowered level to maintain a desired amount of the dissolved gas in the liquid when it is infused into the patient.

Principles of Operation: Dissolved Oxygen

When a gas such as oxygen contacts a liquid like water, some of the oxygen molecules become physically dissolved in the liquid. The dissolved oxygen may be polarographically analyzed and is called the partial pressure of oxygen (abbreviated as pO2). The pO2 is a measure of the force exerted by individual molecules dissolved in solution. The units of measurement for pO2 include millimeters of Mercury (mm Hg.) or Torrecelli (torr). In water and intravenous liquids exposed to air, the pO2 is approximately 159 mm Hg. This amount of dissolved oxygen results from an equilibrium reaction with the partial pressure of oxygen in the air which; under usual barometric pressure of 760 mm Hg., the air is also 159 mm Hg. However; in accordance with Henry's Law, The amount of gas that can be dissolved in a liquid may be increased in two ways: (1) increasing the pressure of a gas above a liquid; and (2) decreasing the temperature of the liquid. In this invention, hyperbaric levels (greater than 760 mm. Hg) of dissolved oxygen results from decreasing the temperature of the liquid during equilibration with a gas such as oxygen to produce supersaturation of the gas and liquid mixture. In this application, the purpose of the gas liquid contact device is to increase the partial pressure of oxygen dissolved in intravenous liquid in order to infuse the liquid to a patient and achieve normal blood oxygenation.

A second factor affecting the amount of oxygen dissolving in a liquid is the temperature of the liquid. As may be seen in Table 1, the solubility of oxygen in water is greatly increased by decreasing the temperature of the liquid. For example, oxygen solubility in water at zero degrees Centigrade is nearly double the amount found in blood plasma at body temperature (38 degrees Centigrade).

TABLE 1

Solubility of Oxygen in Water at Different temperatures:

| | Temperature (Degrees C.) | Oxygen |
|---|---|---|
| Water: | 0 | 0.049 |
| | 20 | 0.031 |
| | 37 | 0.023 |
| Plasma | 38 | 0.024 |

An unexpected discovery of the present invention is that greater than hyperbaric levels of dissolved oxygen may be achieved and maintained in liquids by exposing the liquid to pure oxygen gas and decreasing the temperature of the liquid. Intravenous liquids are currently exposed to room temperatures (approximately 20 degrees Centigrade) and infused into a patient at that temperature. However, the safety of injecting cold intravenous infusions has been well established by the method of inducing mild therapeutic hypothermia. In this method, cold liquid intravenous liquids are directly injected into the vasculature in order to reduce core body temperature to a target of 32 to 34 degrees C., (normal body temperature is 37 degrees C.).

This invention combines the process of therapeutic hypothermia with intravenous supersaturated dissolved oxygen infusions in order to titrate blood oxygen levels to normal or baseline levels.

Physiology of Normal Blood Oxygenation

In blood, oxygen is transported in two forms: (1) physically dissolved in the blood plasma and (2) chemically combined with the hemoglobin contained within red blood cells. The oxygen physically dissolved in blood plasma consists of free oxygen molecules which exert a measurable partial pressure (abbreviated as pO2). Significant differences normally exist between the pO2 of the mixed venous blood (blood traveling towards the lungs to obtain oxygen) and arterial blood (oxygenated blood traveling away from the lungs for distribution throughout the body). In healthy adults with normal cardiopulmonary function, the mixed venous pO2 is about 40 mm Hg. and the arterial pO2 is about 100 mm Hg. Therefore, a primary function of healthy lungs is to allow significant oxygen exchange between inhaled air and blood such that the pO2 continuously increases from 40 mm Hg. to 100 mm Hg. as mixed venous blood traverses the lungs and becomes arterialized.

The second and most substantial way in which oxygen is transported by the blood and delivered to tissue is in the form of oxyhemoglobin. The formation of oxyhemoglobin occurs inside the red blood cells as hemoglobin chemically combines with oxygen molecules. Since the red blood cells remain submerged in the watery plasma, the partial pressure of oxygen dissolved in the plasma (pO2) has effect on the formation of oxyhemoglobin. In essence, the plasma pO2 establishes the pressure gradient which causes free oxygen molecules in the plasma to diffuse inside the red blood cell in the formation of oxyhemoglobin. The hemoglobin percent saturation measurement refers to the percentage of hemoglobin bond sites which exist as oxyhemoglobin. In healthy adults, the normal mixed venous hemoglobin saturation is about 75% at a pO2 of 40 mm Hg. Following oxygen absorption into the blood at the lungs, the arterial hemoglobin saturation is about 97% at a pO2 of 100 mm Hg.

The chemical bond between hemoglobin and oxygen in the formation of oxyhemoglobin is affected by multiple factors. These factors include blood pH, temperature, dissolved carbon dioxide, and 2,3 diphosphoglycerate. The nature of this bond is such that; in mixed venous blood with a pO2 of 40 mm Hg., a small increase in the pO2 may result in a large increase in hemoglobin saturation with oxygen. Therefore, the injection of a super oxygenated liquid into mixed venous blood is intended to result in an increased pO2 and hemoglobin saturation as the intravenous liquid continuously mixes with the blood plasma and red blood cells. In addition, because of the effect of temperature on the chemical affinity between hemoglobin and oxygen, the injection of a relatively cold intravenous liquid at approximately 7 degrees Centigrade (45 degrees F.) will enhance the formation of oxyhemoglobin because of increased chemical bonding affinity between hemoglobin and oxygen.

The total oxygen content of blood is determined by adding the (1) dissolved oxygen with (2) the oxygen chemically combined with hemoglobin. By convention, total oxygen content of blood is expressed in the form of the number of milliliters of oxygen contained in each 100.0 milliliters of blood or volumes percent (abbreviated as vol. %). In mixed venous blood, the oxygen content is approximately 15 volumes percent (15 vol. %.). Arterial blood has an oxygen content of approximately 20.4 vol. %.

The term "oxygen delivery" refers to the optimum amount of oxygen delivered by blood to tissues each minute. Oxygen delivery may be determined by multiplying the arterial oxygen content by the cardiac output and a factor of 10. The normal amount of oxygen delivered to tissues throughout the body is approximately 800.0 to 1000.0 milliliters of oxygen per minute. Therefore, the primary purpose of intravenously injecting a super-saturated dissolved oxygen liquid into the bloodstream is to maintain adequate oxygen delivery to tissues especially when lung impairment exists. A summary of normal values for the process of blood oxygenation may be found in Table 2.

TABLE 2

Normal Values in Blood Oxygenation

| | Mixed Venous Blood | Arterial Blood |
|---|---|---|
| pO2 (mm Hg.) | 40.0 | 100.0 |
| HbO2 per cent Saturation (SO2) | 75% | 97% |
| Oxygen Content (vol. %) | 15 vol. % | 20 vol. % |
| Normal Oxygen Delivery to Tissues per Minute (ml/min) | 800-1000 ml/min. | |

Titration of Blood with Supersaturated Dissolved Oxygen Liquid

Titration refers to a method of determining the smallest amount of a substance required to achieve a desired effect in a chemical reaction. When a super-oxygenated liquid is intravenously injected into the bloodstream, the goal is to increase the mixed venous blood oxygen content to levels which will maintain adequate oxygen delivery to tissues. Basically, this method may be used to supplement the oxygenation function of the lungs when the normal lung function is impaired by disease.

In order to achieve adequate oxygen delivery to tissues using the method of intravenously injecting oxygenated liquids, two variables may be manipulated. These variables are the (1) partial pressure of oxygen dissolved in the infused liquid (abbreviated as the pO2) and; (2) the flowrate of fluid injection. The combination of these two variables will ultimately determine the net change in blood oxygen content and; subsequently, oxygen delivery to tissues. Following injection into the bloodstream, the mixing of the oxygenated liquid with blood will result in significant increases in the partial pressure of oxygen dissolved in blood plasma, which in turn, will result in increased hemoglobin saturation with oxygen. The increases in both the dissolved pO2 and the oxyhemoglobin percent saturation raise the oxygen content of mixed venous blood, and subsequently, oxygen delivery to tissues. Further, the infusion of a cold liquid will decrease the oxygen requirements of tissues, decrease the carbon dioxide production of tissues, and decrease the overall tissue metabolic rate.

Following injection into the bloodstream, it is believed that the mixing of the oxygenated liquid with blood will result is significant increases in the partial pressure of oxygen dissolved in blood plasma which in turn will result in increased hemoglobin saturation with oxygen. The increases in both the dissolved pO2 and the oxyhemoglobin percent saturation raise the oxygen content of mixed venous blood, and; subsequently, the oxygen content of arterial blood is increased. Therefore, an overall net increase of oxygen delivery to tissue occurs while the oxygen requirements for tissues are simultaneously decreased via a decreased metabolic rate. The variables of fluid infusion flowrate and the pO2 of the liquid may be manipulated to maintain a rate of oxygen delivery to tissues of 800.0 to 1000.0 milliliters of oxygen per minute.

The oxygenated liquid may be injected into the bloodstream as a continuous infusion or injected as a bolus during emergencies. During continuous infusions, fluid flow rates of 30.0 to 500.0 milliliters per hour may be used for adults. Because of the relatively small volume of liquid infused per minute during a continuous infusion, it is expected that the oxygenated liquid pO2 must be significantly increased (compared to the normal liquid pO2 of 159 mm Hg.) in order to appreciably increase the blood oxygen level. A continuous infusion of the oxygenated liquid may be beneficial when supplemental blood oxygenation is required to support moderate lung impairment from a disease like pneumonia. This type of supplemental oxygenation may be life-saving when lung impairment results in hypoxemia despite traditional treatment with oxygen inhalation.

The injection of a bolus solution refers to the relatively rapid infusion of a large volume of liquid in a short period of time. During a bolus injection, 50.0 to 200.0 milliliters of oxygenated liquid could be infused over a period of several minutes. The injection of a bolus of oxygenated liquid may be extremely useful in emergency situations like choking where the breathing passages are completely blocked and no oxygen exchange occurs in the lungs. Left untreated, tissue death will occur in minutes due to hypoxia. On the other land, a bolus injection of oxygenated liquid containing a high pO2 provided immediate blood oxygenation which would otherwise be impossible until the breathing passages were cleared.

During a bolus injection, caution should be used to ensure that the supersaturated liquid is infused over a sufficient period of time, such as several minutes duration, to allow gradual mixing of the patients blood with supersaturated liquid. Sudden infusions of a large volume of supersaturated fluid should be avoided to prevent the dissolved gas from forming emboli within the vasculature.

Factors Affecting the Titration Level

The optimal pO2 and infusion rate of the oxygenated liquid may vary from one patient to another because of individual differences in disease state, physiological function, and severity of illness. However the following factors must be considered when blood oxygen levels are titrated with oxygenated liquid infusions:

1 Cardiac Output
2 Oxygen Content of Mixed Venous Blood
3 Oxygen Content of Arterial Blood
4 Hemoglobin Concentration
5 Fluid Intake and Output
6 Oxygen Consumption
7 Hemoglobin Affinity for Oxygen (p50)
8 Fractional Inspired Oxygen Concentration (FI02)
9 Matching of Ventilation and Perfusion
10 Interpulmonary Shunt
11 Electrolytes (Sodium, Potassium, Chloride)

The efficacy of titrating blood with oxygenated liquids may be determined by conventional monitoring techniques such as periodic blood gas analysis, oximetry, transcutaneous oxygen analysis, and fluorescent optode measurement of blood gases.

FIG. 1 illustrates one embodiment for producing and administering an intravenous liquid. It is understood that other embodiments may include the same or different elements depending upon the specific demands of the system. This system includes a sterile intravenous (IV) bag 28 with an outlet having a spike connector 30. A variety of different non-blood liquids may be contained in the bag 28, including but not limited to saline, dextrose and water, and Ringer's lactate liquid. A line extends from the connector 30 into a gas-liquid contact device 40. The gas-liquid contact device 40 may include a variety of different shapes and sizes. FIG. 1 includes the gas-liquid contact device 40 being a burette with a cylindrical shape with a volumetric graduation along its length with a roller clamp valve 48 at a lower end. A roller valve 34 is positioned along the line to control an amount of liquid that exits from the bag 28 such that a volume of liquid from the bag 28 may be infused into the gas-liquid contact device 40.

The system is further configured to introduce a gas into the gas-liquid contact device 40. This is accomplished through a gas blender 20 that is connected to a flowmeter 24. The flowmeter 24 in turn connects to a gas conducting tubing 26 that includes an inlet four-way stopcock valve 16. A tube 53 extends between the valve 16 and the gas-liquid contact device 40. The tube 53 is arranged so that gas from the gas conducting tubing 26 flows through the inlet four-way stopcock valve 16 and into a first end of the tube 53. The opposing second end of the tube 53 includes a bubble diffusing head 50 that is positioned beneath the surface of the liquid contained in the gas-liquid contact device 40. The gas-liquid contact device 40 connects to an adjustable stopcock valve outlet and filter 37. The adjustable stopcock valve outlet and filter 37 may operate as a vent in some embodiments.

A refrigeration unit 46 is positioned at the gas-liquid contact device 40 to cool the liquid. In one embodiment, the refrigeration unit 46 extends around a portion or entirety of an exterior of the gas-liquid contact device 40. Another embodiment includes the refrigeration unit 46 positioned at least partially within an interior of the gas-liquid contact device 40, but away from an interior space that contains the liquid. Still another embodiment includes the refrigeration unit 46 positioned within the interior space that contains the liquid. In one embodiment, the refrigeration unit 46 is configured to contain a refrigerant. A variety of different refrigerants may be used, including ice and water, cold pack gels, Freon, and others. The refrigeration unit 46 may also include thermal insulation that extends around a portion or entirety of the gas-liquid contact device 40 to assist in maintaining the liquid at the desired lower temperature.

A Murphydrip tube 80 is positioned at a bottom of the gas-liquid contact device 40. The Murphydrip tube 80 is attached to tubing 58 via a roller clamp valve 48 with the valve 48 positioned to control the flow rate from the Murphydrip tube 80 into the tubing 58. The tubing 58 is thereafter connected to a bubble filter 54. In some embodiments, a pump 56 is positioned downstream from the bubble filter 54 to regulate the flow rate.

A bubble detector 60 is positioned below and connected with the bubble filter 54 or pump 56. In some embodiments, the bubble detector 60 is connected to an alarm, an automatic shutoff system, or both to prevent infusion of gas bubbles. The bubble detector 60 is connected to tubing 64 which in turn connects to a standard intravenous central line catheter 74.

The components that come into direct contact with the liquid or gas may be made of a rust-resistant, non-corrosive substance which is not reactive with oxygen. In some embodiments, the inside layer 52 of the gas-liquid contact device 40 may be coated with a substance to minimize bubble nucleation thresholds and reduce bubble formation in the gas saturated liquid, such as benzalkonium heparin or small quantities of ethanol.

The various tubing may be coated with a non-toxic gas diffusion resistant coating, such as, for example, Fluid Hi Float R. The tubing may also be covered with a substance that maintains the temperature of the liquid, such as Neoprene R or Mylar R.

Figure 2:
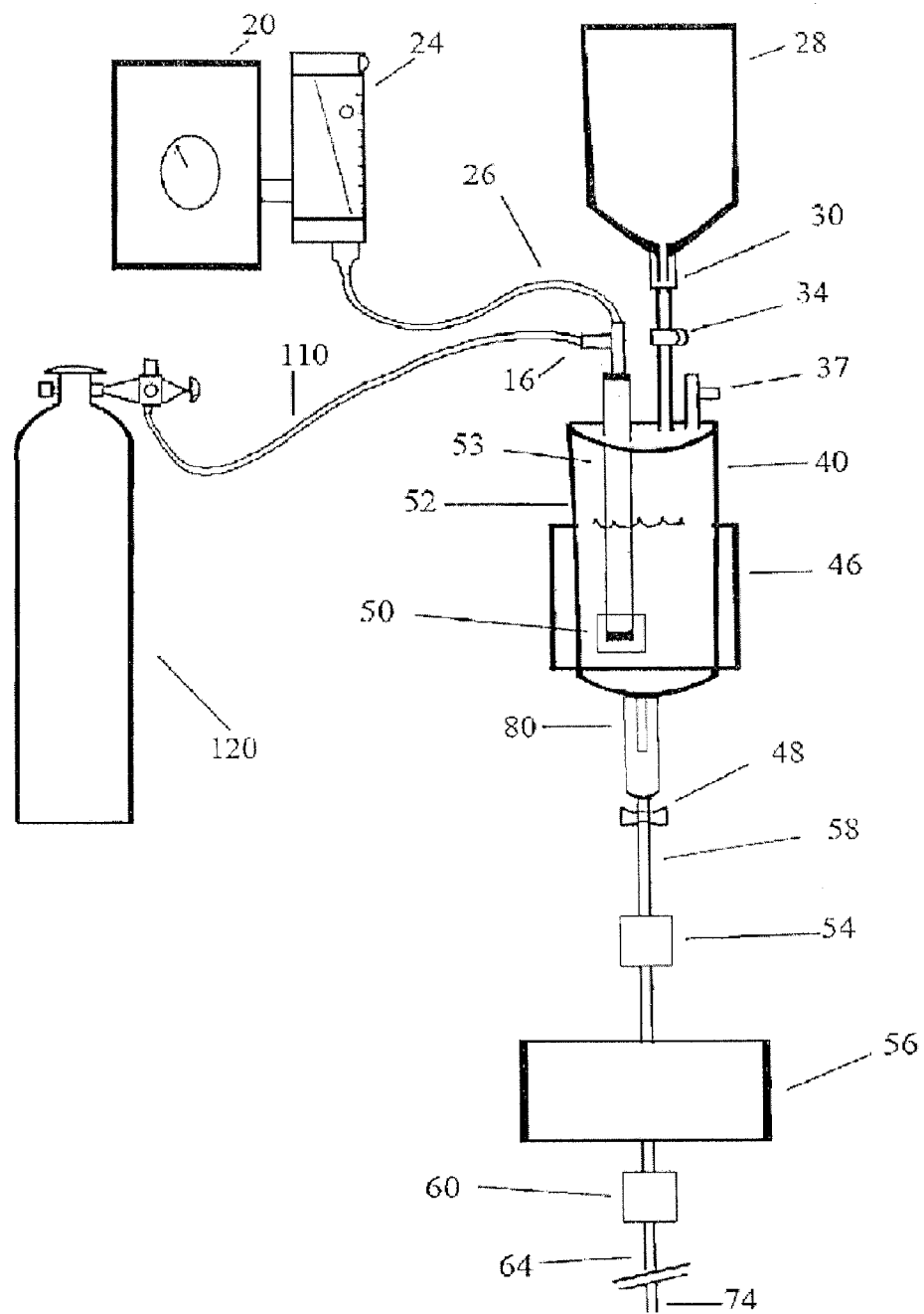
FIG. 2 is a schematic view of a system for dissolving gases in a cooled liquid at ambient pressure.

As illustrated in FIG. 2, the system may also include a high pressure tank 120 connected through a regulator and tubing 110 to the inlet four-way stopcock valve 16. The tank 120 includes a different gas than is introduced through the gas blender 20 and flowmeter 24.

The gas introduced into the gas-liquid contact device 40 may include one or more different types of gases. In one embodiment using the system of FIG. 2, oxygen is introduced into the system through the blender 20/flowmeter 24, and a second gas is introduced from the tank 120. The different gas introduced through the tank 120 may include but are not limited to oxygen, carbon monoxide, helium, and ozone.

The term "gas" is used herein to mean one or more of the various types of gases that may be placed into contact with the liquid.

The gas selected for mixing may be based upon individual patient needs and may be rapidly mixed and administered using a variety of systems. In one embodiment, oxygen may be mixed with liquid and infused to support oxygenation and allow weaning of mechanical ventilation parameters to minimize lung damage. In another embodiment, helium may be mixed with the liquid to decrease liquid viscosity and minimize bubble nucleation formation.

The systems illustrated in either of FIGS. 1 and 2 may be used to produce and administer the intravenous liquid. Prior to beginning the process of preparing the intravenous liquid, it may be desirable to remove dissolved gases already present in the liquid to prevent the inadvertent compression of other gases. Such removal may be accomplished by, for example, boiling or chemical means. In one embodiment that includes oxygen being dissolved into the liquid, the liquid may first have all dissolved gases removed to prevent the inadvertent compression of gases such as nitrogen. Further, the gas-liquid contact device 40 and the Murphydrip tube 80 may be coated with a small quantity of ethanol to minimize gas bubble formation in the liquid.

The method includes the liquid being slowly infused from the IV bag 28 into the gas-liquid contact device 40 to reach the desired level or volume of liquid. This may include insertion of the spike connector 30 into the outlet of the bag 28. The valve 34, which is closed prior to insertion of the spike 30, is subsequently opened to allow the liquid to fill the interior of the gas-liquid contact device 40 to the desired level. In one embodiment, the liquid is infused slowly to minimize bubble formation near the Murphydrip tube 80. In one embodiment for an adult patient, an initial liquid volume of about 100 ml. is infused into the gas-liquid contact device 40.

Following infusion of the liquid into the gas-liquid contact device 40, the gas is supplied to the gas blender 20 via high pressure gas conducting tubing (not illustrated). The desired gas concentration percentage and subsequent partial pressure to be dissolved in the liquid contained in the gas-liquid contact device 40 is selected on the gas blender 20. Once the desired gaseous partial pressure is selected on the gas blender 20, the gas travels from the gas blender 20 and flowmeter 24, through gas tubing 26 and 53, and into the gas-liquid contact device 40. Additional gas may be introduced in a like manner through the tank 120 and tubing 110 and 53. As the gas bubbles through the gas bubble diffusing head 50 at the end of the tubing 53, the gas mixes with the liquid contained in the gas-liquid contact device 40.

The temperature of the liquid in the gas-liquid contact device 40 at the time the gas is introduced may vary. In one embodiment, the liquid is previously cooled prior to the initial contact with the gas. The cooling may be done at a location other than the gas-liquid contact device 40 (e.g., the liquid is refrigerated prior to introduction into the device 40), or may be cooled in the device 40 by the refrigeration unit 46. In another embodiment, the liquid is at about room temperature when introduced into the device 40 and subsequently cooled at some point by the refrigeration unit 46.

At some point in time, the temperature of the liquid is decreased which increases the amount of dissolved gas in the liquid. In one embodiment, the temperature of the liquid is decreased to less than about 70° F. In one embodiment, the temperature of the liquid is decreased to less than about 55° F. In another embodiment, the temperature is decreased to less than about 45° F. Another embodiment includes decreasing the temperature to less than about 40° F.

In one embodiment that has gas supplied just through the blender 20, the flow rate of the gas is adjusted to about 3 L/min and allowed to bubble through the liquid for about 20 minutes. After contact with the liquid, the gas may be vented from the gas-liquid contact device 40 at the stopcock valve 37. The liquid is at ambient pressure during contact with the gas. The valve 37 may be adjusted to regulate the pressure within the gas-liquid contact device 40. In one embodiment, the initial position of the valve 37 is fully open to ambient air to allow venting of the inject gas. The valve 37 may remain fully open during the entire process. The valve 37 may also be adjusted to provide the desired internal pressure and allowing gas within the device 40 to be vented. In one embodiment, a manometer is coupled to the valve 37 to accurately regulate the internal pressure of the gas-liquid contact device 40.

The gas may be filtered to prevent contamination of the liquid both at entry into the gas-liquid contact device 40, and upon exiting the gas-liquid contact device at valve 37.

The liquid remains in contact with the gas in the gas-liquid contact device 40 until the liquid is supersaturated with the dissolved gas. In one embodiment, if oxygen is the desired gas to be mixed with the liquid, the oxygen and liquid are mixed within the gas-liquid contact device 40 until the partial pressure of the gaseous oxygen dissolved in the liquid is increased to greater than 760 mmHg.

After the desired gas has mixed with the liquid, the flowmeter 24 is turned off and the valve 37 is closed to ambient air. The gas flow should be stopped whenever liquid in the gas-liquid contact device 40 is empty to prevent inadvertent infusion of gas into the vasculature. In one embodiment, mixing of the gas and liquid occurs intermittently with stoppage of gas flows at designated time periods.

After bubbling the gas through the liquid, the liquid is maintained in the gas-liquid contact device 40 which prevents contamination with the external environment.

Following the mixing and solvation of the gas and liquid in the gas-liquid contact device 40, the liquid flows through the Murphydrip tube 80. The liquid flow rate out of the gas-liquid contact device 40 and the Murphydrip tube 80 is controlled by the roller clamp valve 48. The liquid flows through the Murphydrip tube 80 through tubing 58 and the bubble filter 54. A pump 56 may regulate the infusion flowrate. The liquid than travels past a bubble detector 60 and tubing 64 with the bubble detector 60 providing an alarm and automatic shutoff to prevent accidental gas infusion. The liquid than travels into the standard intravenous central line catheter 74.

The liquid remains at or near the lowered temperature to maintain the gas partial pressures at the selected values while being administered to the patient. The liquid may be delivered relatively quickly after exiting the gas-liquid contact device 40 thereby maintaining the lowered temperature.

One or more sections of the tubing 58, 64 may be coated on the exterior to preserve dissolved gas tensions in the liquid. A non-toxic type of gas diffusion resistant coating such as Fluid Hi Float R may be used to coat the tubing 58, 64 to prevent gas diffusion out of the liquid.

Figure 3:
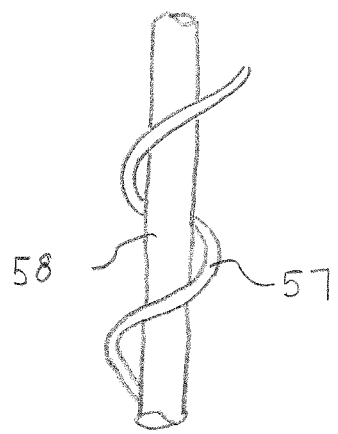
FIG. 3 is a side view of a cooling device wrapped around a tube carrying a liquid.
Figure 4:
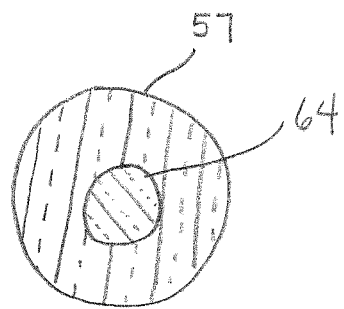
FIG. 4 is a sectional view of a tube carrying a liquid positioned within an interior of a cooling device.

The tubing 58, 64 may be also be configured to maintain the liquid at the lowered temperature during delivery to the patient. In one embodiment, the tubing 58, 64 is covered with a substance such as Neoprene R. In one embodiment as illustrated in FIG. 3, the tubing 58, 64 is wrapped or braided with a tube 57 containing refrigerant. Another embodiment as illustrated in FIG. 4 includes the tubing 58, 64 positioned inside a tube 57 containing a refrigerant.

Figure 5:
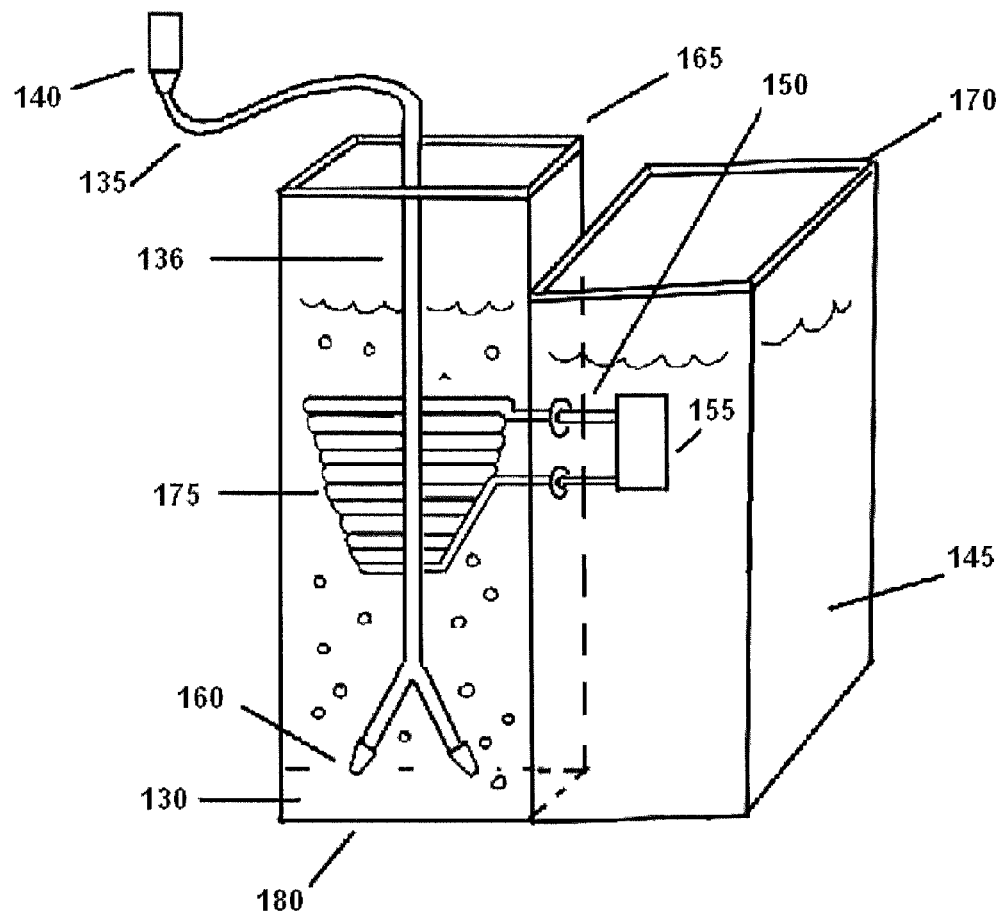
FIG. 5 is a schematic view of a system for dissolving a gas in a cooled liquid at ambient pressure.

FIG. 5 illustrates another embodiment of producing an intravenous liquid that includes a mixing gas-liquid contact device 130 that contains the liquid and a refrigerant chamber 145. Gas is introduced into the mixing gas-liquid contact device 130 through a gas flowmeter 140 and tubing 135. Tubing 135 extends into the mixing gas-liquid contact device 130 and is positioned with a distal end remaining beneath the surface of the liquid therein. In some embodiments, tubing 135 connects to at least one bubble diffusing head 160 that remains beneath the surface of the liquid. An outlet 180 is located on the bottom of the mixing gas-liquid contact device 130. A refrigeration coil 175 is within the mixing gas-liquid contact device 130 and in contact with the liquid. The refrigeration coil 175 is connected to tubing 150 that extends between the mixing gas-liquid contact device 130 and a refrigerant chamber 145. A pump 155 connected to the tubing 150 is located in the refrigerant chamber 145. Both the mixing gas-liquid contact device 130 and the refrigerant chamber 145 may include removable covers 165 and 170 respectively.

In use, intravenous liquid is filled into the mixing gas-liquid contact device 130 and contained there at ambient pressure. The gas flowmeter 140 controls an amount of gas introduced into the system. Additional gas may be introduced through a separate tank in a similar manner to that illustrated in FIG. 2. The gas flows through the tubing 135 and the one or more bubble diffusing heads 160. As the gas exits through the bubble diffusing heads 160 and mixes with the liquid in the mixing gas-liquid contact device 130 until the liquid is supersaturated with the dissolved gas. Contact between the gas and the liquid is maintained until a supersaturated liquid having hyperbaric gaseous partial pressures is produced.

The temperature of the liquid in the mixing gas-liquid contact device 130 is lowered to increase the amount of dissolved gas. In one embodiment, the temperature is lowered to about 55° F. or less. In another embodiment, the temperature is lowered to about 45° F. The temperature of the liquid may be lowered prior to delivery of the gas, during the delivery of the gas, after delivery of the gas, or combinations thereof.

To decrease the temperature, the separate refrigerant chamber 145 supplies refrigerant to the mixing gas-liquid contact device 130 via tubing 150. The tubing 150 is routed from the refrigerant chamber 145 into the interior of the mixing gas-liquid contact device 130 where it forms a refrigerant coil 175. A pump 155 in the refrigerant chamber 145 pumps the refrigerant through the tubing 150 and the refrigerant coil 175 in the mixing gas-liquid contact device 130. The refrigerant remains within the interior of the tubing 150 and the refrigerant coil 175 and does not directly contact the liquid contained within the mixing gas-liquid contact device 130. After the refrigerant flows through the coil 175, it is pumped through the tubing 150 and back to the refrigerant chamber 145 for re-cooling. Various types of refrigerant may be used, including but not limited to ice packs, gels, and Freon.

Once the desired amount of gas is dissolved into the liquid, the liquid is directed from the mixing gas-liquid contact device 130 through an outlet 180 for intravenous delivery. In some embodiments, IV tubing is coupled to outlet 180 and is configured to receive the supersaturated liquid for delivery to the patient. Cooling methods as described above in FIGS. 3 and 4 may provide for keeping the liquid at a reduced temperature.

Spike Connector

The present application discloses the mixing of a gas with a cooled liquid at ambient pressure to form a supersaturated liquid. This discovery now makes it possible to use existing equipment in combination with novel aspects disclosed in this application to form and deliver the liquid to the patient. One embodiment provides for forming the liquid in a container such as an IV bag.

Figure 6:
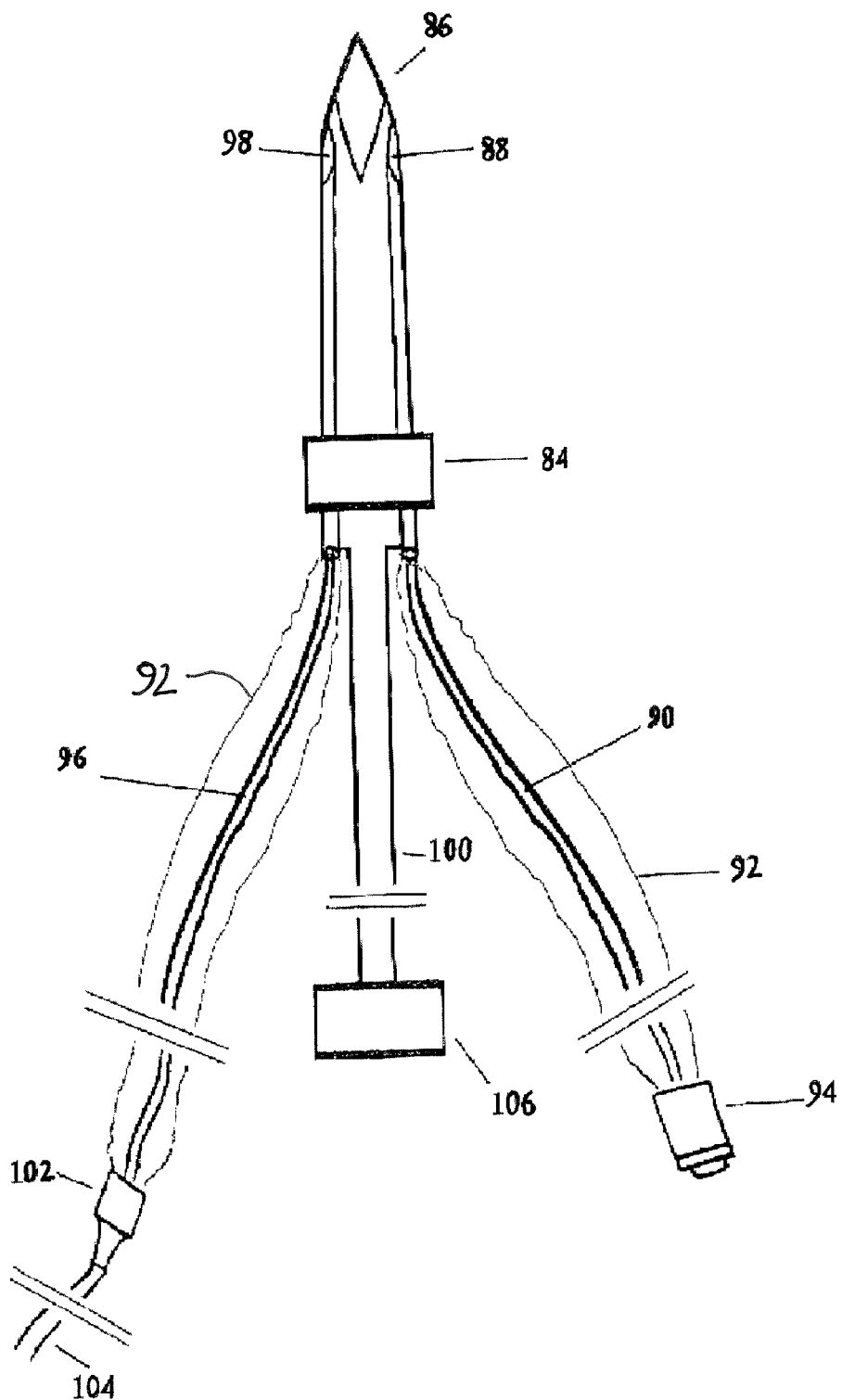
FIG. 6 is a side view of a connector for connecting with a liquid container.
Figure 7:
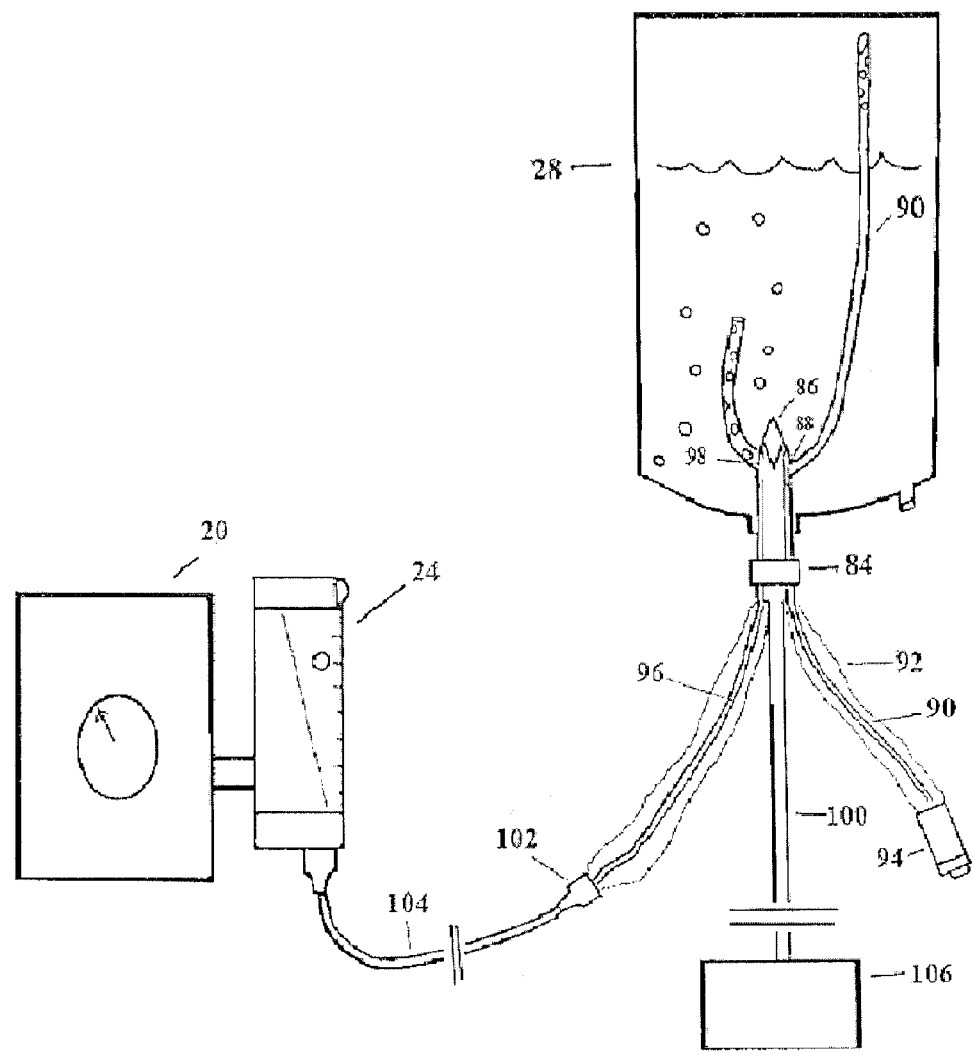
FIG. 7 is a schematic view of a connector inserted within a container for dissolving a gas in a cooled liquid at ambient pressure.

FIGS. 6 and 7 illustrate a spike connector 84 that is used with a liquid container, such as an IV bag 28 to practice the methods disclosed in the application. The connector 84 is configured to be inserted into an outlet of the IV bag 28 and provides for the mixing of the gas with the liquid directly within the bag 28 itself. As illustrated in FIG. 6, the connector 84 includes a leading end that is inserted into the container and an opposing trailing end that remains on the exterior of the container. The leading end may include a pointed tip to facilitate insertion into the bag. The connector 84 includes a liquid port 86 to remove the mixed liquid from the container 84. The connector 84 also includes a vent tube port 88 to accommodate a vent tube 90 and a gas insertion port 98 to accommodate a gas insertion tube 96. Each of the ports extends from generally the leading end to the trailing end of the connector 84.

The liquid port 86 provides for removing the mixed liquid from the container 28. Tubing 100 is connected to the port 86 and extends outward from the trailing end of the connector 84. A pump 106 may be positioned along the tubing 100.

The vent tube 90 may be attached to the connector 84 at the time of insertion into the container, or may be attached after the insertion. The vent tube 90 is moved along the vent tube port 88 and into the container until the leading end is positioned above the liquid level. This positioning is illustrated in FIG. 7. A plastic sheath 92 may extend around the tube 90 where is extends outward from the connector 84 to prevent contamination of the tube 90. The plastic sheath 92 also maintains the container 28 as a closed, sterile system. The trailing end of the tube 90 is connected to a gas filter 94.

The gas insertion tube 96 may be attached to the connector 84 at the time of insertion into the container 28, or may be attached after the connector 84 is inserted into the container 28. The tube 96 is moved through the gas insertion port 98 with a leading end positioned below the level of the liquid towards a bottom of the container 28. In one embodiment, the leading end is positioned about ¼ of the distance from the bottom of the container 28. A plastic sheath 92 covers the tube 96 to maintain sterility of the liquid in the container 28. Further, a connector 102 may be positioned at the trailing end of the tube 96 to connect with the gas tubing 104.

The liquid in the container 28 may be cooled prior to insertion of the connector 84. In one embodiment, the container is stored in a refrigerator to chill the liquid to the necessary temperature, such as about 55° F. or less, 45° F., or less than 40° F. as described above. Cooling mechanisms, such as ice packs, may be attached to the exterior of the container 28 to keep the temperature of the liquid at the desired level and/or to cool the liquid to the desired temperature. In another embodiment, the temperature of the liquid is cooled after insertion of the connector 84.

In use, the connector 84 is inserted into the outlet of the container 28. The leading end is inserted through the outlet and into the interior of the container 28 with the trailing end remaining on the exterior of the container 28. The tube 96 is moved through the gas insertion port 98 to extend into the liquid. Further, the gas tubing 104 is attached to the connector 102. Likewise, the tube 90 is moved through the vent tube port with the leading end placed above the level of the liquid in the container 28.

The gas blender 20 is adjusted to the desired gas concentration and the flowmeter 24 is adjusted to the desired amount. In one embodiment, the flowmeter 24 is adjusted to a gas flow of about 3 L/min. The gas flows through the tubing 104, 96 and into the interior of the container 28 where it exits into contact with the liquid. In one embodiment, the gas bubbles through the liquid for about 20 minutes. Excess gas in the container 28 is vented through the tube 90 to the exterior. After the mixing is complete, the flowmeter 24 is turned off and the tube is clamped or otherwise placed in an off position.

The mixed liquid is removed from the container 28 through the liquid port 86, through tubing 100, and past the pump 106 for infusion into the vasculature of the patient. In some embodiments, additional tubing is coupled to the outlet of pump 106 and to a bubble detector which can monitor for bubbles in the liquid. The bubble detector may be connected to an alarm and automatic shutoff system to prevent inadvertent gas bubble infusion into the patient. The liquid infusate travels through the additional tubing, past the bubble detector, and into a standard intravenous central line catheter.

In one embodiment, the spike connector 84 is used for mixing a gas with a cooled liquid at ambient pressure as described above. The connector 84 may also be used for various other contexts of use.

Testing Results

The devices and methods described herein were used to garner reproducible test results. FIGS. 8a-8f illustrate the results from testing on four different animals: S1—FIG. 8a; S2—FIG. 8b; S4—FIGS. 8c; and S5—FIG. 8d. Each animal had infusions of supersaturated dissolved oxygen for 1 hour. In this study, the liquid was cooled in a mixing gas-liquid contact device and cooled by moving a refrigerant in a cooling chamber through a coil (as illustrated in the embodiment of FIG. 5).

FIGS. 8e and 8f illustrate the results from the infusions on a control animal (S3). The control animal had a first round of testing with infusions of Ringer's lactate without supersaturated dissolved oxygen (FIG. 8e), followed by a second round of infusions of supersaturated dissolved oxygen (FIG. 8f).

Each of the test subjects were intravenously infused with a supersaturated dissolved oxygen liquid and experienced induced hypothermia based on reduced core body temperature. As shown in FIGS. 8a, 8b, 8c, and 8d, upon receiving this treatment, all test subjects showed improved oxygenation, based on the arterial blood gas data of the partial pressure of $O_2$ and the $O_2$ saturation. In addition, all test subjects showed improved ventilation based on the decreased partial pressure of $CO_2$, decreased $EtCO_2$, and increased pH. These changes occurred with no changes to the ventilator settings and the subject had no spontaneous breathing throughout the study. The control study (S3-R1) showed insignificant changes in blood gases during infusion of Ringers lactate solution without supersaturation of dissolved oxygen.

In one embodiment, the system included a saline liquid that had an initial temperature of 68.4° F. at an ambient pressure of 710 mm Hg. The ambient temperature of the lab was 72° F. An 85% oxygen gas was bubbled through the liquid at a flow rate of 3 L/min for 20 minutes. During this time, the liquid temperature was reduced from the 68.4° F. starting temperature to a final temperature of 66.4° F. The cooling of the liquid was likely caused due to evaporative cooling of the liquid. At the end of the process, the liquid had a dissolved oxygen partial pressure of 795 mm. Hg. In this embodiment, the dissolved oxygen tension was 85 mm Hg greater than atmospheric pressure.

The liquid with the lowered temperature may be infused into a patient with a normal body temperature to induce mild therapeutic hypothermia. This occurs when the patient's body temperature is lowered to about 32° C.-34° C.

The liquid may also be infused into the patient as a method of respiration (gas exchange). One embodiment includes intravenously infusing the liquid with dissolved oxygen into the patient and inducing mild therapeutic hypothermia. This results in improving the oxygen transport of blood by increasing the chemical affinity between hemoglobin and dissolved oxygen resulting from decreased temperature and decreased blood dissolved carbon dioxide levels. This may also result in decreasing the dissolved carbon dioxide partial pressure in blood. This may also result in decreasing the tissue metabolic rate (rate of oxygen consumption demand and carbon dioxide production) via mild therapeutic hypothermia and infusion of cold, supersaturated dissolved oxygen liquids.

The liquid may also be used in a method for creating and administering a resuscitation liquid. Another use is for a method for altering pulmonary blood flow in the lungs. Another use may include a method to decrease acute lung injury from positive pressure ventilation and oxygen inhalation consisting of supportive intravascular gas exchange. These methods may each be used with intravenously infusing the cooled liquid into the patient and inducing mild therapeutic hypothermia. Another use may be to infuse procured organs with cold, supersaturated dissolved oxygen solutions in order to preserve organs by decreasing the tissue metabolic rate and increasing the oxygen availability to tissues within the organs.

The devices and methods may be used for a variety of medical applications. Examples include but are not limited to: oxygen therapy; regulating pulmonary blood flow; decrease pulmonary vascular resistance; improve gas exchange within the lung; use as an antimicrobial agent due to liquids containing dissolved gases such as oxygen, either singly or in combination, to induce microbial toxicity (may be useful for anaerobic microbes such as bacteria, fungi, some forms of *Mycoplasma*, and some viruses); use for rescue treatment of resuscitation liquid for cardiac arrest, respiratory failure, and oxygenation failure in acute diseases such as asthma and adult respiratory distress syndrome; adjusting the viscosity and solubility of intravenous liquids by regulating the gas composition and temperature of the liquids; regulating the partial pressure differentials within tissue, including the diffusion driving pressures, to decrease the distance for gaseous diffusion; improving blood and tissue oxygenation; induction of mild therapeutic hypothermia as reflected by decreases in core body temperature. The system may also provide for adjustment of the viscosity and the solubility of the liquid by regulating a gas composition of the liquid.

In the various methods, the contact between the liquid and gas is controlled to dissolve the desired amount of gas into the liquid. The amount of dissolved gas can be controlled by one or more parameters, such as but not limited to: type of liquid, type of gas, temperature of the liquid, the gas flow rate, amount of time the gas is in contact with the liquid. Controlling the desired partial pressure of oxygen in the liquid allows the partial pressure of the gas to be titrated according to an individual patient's needs. This may avoid exposure to excessive gas concentrations. In one embodiment, the gas dissolved in the liquid is selected to infuse the liquid with a precise dissolved gas partial pressure and achieve normal blood oxygen levels for a patient.

Co-pending U.S. patent application Ser. No. 13/410,181 entitled Devices and Methods for Aerosol Therapy Using Hyperbaric Tonometry and filed on the same day as the present application discloses devices and methods for making a supersaturated liquid and administering the liquid to a patient, and is hereby incorporated by reference in its entirety.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A method of treating a patient, comprising:
intravenously infusing into the patient a non-blood liquid supersaturated with oxygen gas;
maintaining the supersaturated liquid at a low temperature while infusing the liquid into the patient so as to decrease a core body temperature of the patient from a pre-infusion baseline temperature to induce mild therapeutic hypothermia in the patient; and
adjusting a flow rate of the oxygen gas into the non-blood liquid while the liquid is stored in a gas-liquid contact device and dissolving a desired amount of the oxygen gas in the liquid prior to intravenously infusing the non-blood liquid supersaturated with the oxygen gas into the patient.

2. The method of claim 1, wherein the liquid is at ambient pressure while being intravenously infused into the patient.

3. The method of claim 1, wherein the liquid is less than about 70° F. while being intravenously infused into the patient.

4. The method of claim 1, wherein the supersaturated liquid increases oxygen delivery to tissue while simultaneously decreasing tissue metabolic rate of oxygen consumption and carbon dioxide production.

5. The method of claim 1, wherein the intravenous infusion of the supersaturated liquid induces the mild therapeutic hypothermia, producing intravascular gas exchange and increasing the chemical affinity between hemoglobin and dissolved oxygen.

6. The method of claim 1, further comprising adjusting a flow meter on a feed tube leading into the contact device and adjusting the flow rate of the oxygen gas.

7. The method of claim 1, further comprising continuously providing the flow of the oxygen gas into the contact device prior to intravenously infusing the non-blood liquid supersaturated with the oxygen gas into the patient.

8. A method of treating a patient comprising:
supersaturating an intravenous non-blood liquid with dissolved oxygen gas;
decreasing the temperature of the liquid and increasing a concentration of the gas dissolved in the liquid;
infusing the supersaturated liquid at the decreased temperature intravenously into the patient to decrease a core body temperature of the patient from a pre-infusion baseline temperature so as to induce mild therapeutic hypothermia; and
adjusting a gas blender and flow rate of the oxygen gas supplied to the non-blood liquid and obtaining a desired gaseous partial pressure.

9. The method of claim 8, wherein decreasing the temperature of the liquid includes decreasing the temperature to less than about 55° F.

10. The method of claim 8, wherein supersaturating the liquid with the dissolved oxygen gas occurs at ambient pressure.

11. The method of claim 8, wherein supersaturating the liquid with the dissolved oxygen gas occurs within an IV bag.

12. The method of claim 8, further comprising selecting a desired gaseous partial pressure and adjusting the gas blender and a flow meter accordingly that feeds the oxygen gas to the non-blood liquid.

13. The method of claim 8, wherein infusing the supersaturated liquid at the decreased temperature intravenously into the patent further comprises infusing a first portion of the supersaturated liquid into the patient while a second portion remains within a gas-liquid contact device where the oxygen gas is dissolved into the non-blood liquid.

14. A method for intravenous liquid therapy comprising
mixing a gas with a non-blood liquid while the non-blood liquid is at a decreased temperature of less than about 55° F. and at ambient pressure;
maintaining the liquid in contact with the gas at ambient pressure and at less than about 55° F. until the partial pressure of the gas in the liquid reaches greater than 760 mmHg;
intravenously introducing the liquid into a patient while maintaining the liquid at less than about 55° F. and the partial pressure of the gas greater than 760 mmHg; and
adjusting a gas blender and flow rate of the gas supplied to the non-blood liquid and obtaining a desired gaseous partial pressure of the gas in the liquid.

15. The method of claim 14, further comprising initially introducing the gas into the liquid when the liquid is less than about 55° F.

16. The method of claim 14, wherein the gas is a mixture of two or more different gases.

17. The method of claim 14, wherein the gas is selected from the group consisting essentially of oxygen, helium, ozone, and carbon monoxide.

18. The method of claim 14, wherein the decreased temperature is less than about 45° F.

19. The method of claim 14, further comprising activating a refrigeration unit and reducing the liquid to less than about 55° F. after introducing the gas into the liquid.

20. The method of claim 14, further comprising cooling the liquid between when the liquid is removed from a container and intravenously introducing into the patient.

21. The method of claim 14, further comprising adjusting the gas blender and a flow meter that feeds the gas to the non-blood liquid to obtain a desired gaseous partial pressure of the gas in the non-blood liquid.

22. The method of claim 14, wherein intravenously introducing the liquid into the patient further comprises introducing a first portion of the liquid into the patient while maintaining the liquid at less than about 55° F. and the partial pressure of the gas greater than 760 mmHg while a second portion of the liquid remains within a gas-liquid contact device where the gas is mixed with the non-blood liquid.

23. A method of treating a patient, comprising:
supersaturating a non-blood liquid with dissolved oxygen gas by adjusting a flow rate of the oxygen gas into the non-blood liquid while the liquid is stored in a gas-liquid contact device and dissolving a desired amount of the oxygen gas in the liquid;
intravenously infusing into the vasculature of the patient the non-blood liquid supersaturated with the oxygen gas while the liquid is at a low temperature; and
infusing the liquid into the vasculature so as to decrease a core body temperature of the patient from a pre-infusion baseline temperature to induce mild therapeutic hypothermia in the patient and produce intravascular gas exchange due to diffusion upon mixing of the liquid and blood in the vasculature to increase the chemical affinity between the blood and dissolved oxygen in the liquid, the liquid also configured to decrease the dissolved carbon dioxide partial pressure in the blood.

24. The method of claim 23, further comprising decreasing a tissue metabolic rate of oxygen consumption and carbon dioxide production.

25. The method of claim 23, further comprising causing an increase in a pH level of the patient based on arterial blood gas data.

* * * * *